United States Patent
Grosser

(10) Patent No.: US 6,477,229 B1
(45) Date of Patent: Nov. 5, 2002

(54) RADIATION THERAPY PLANNING

(75) Inventor: Karl-Heinz Grosser, Heidleberg (DE)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 29 days.

(21) Appl. No.: 09/653,659

(22) Filed: Aug. 31, 2000

(30) Foreign Application Priority Data

May 12, 2000 (DE) .......................................... 100 23 158

(51) Int. Cl.[7] ................................................. A61N 5/10
(52) U.S. Cl. ......................................................... 378/65
(58) Field of Search ............................. 378/64, 65, 151

(56) References Cited

U.S. PATENT DOCUMENTS

| | | | |
|---|---|---|---|
| 5,663,999 A | 9/1997 | Siochi | 378/65 |
| 5,724,403 A | 3/1998 | Siochi et al. | 378/150 |
| 5,751,781 A * | 5/1998 | Brown et al. | 378/65 |
| 5,818,902 A | 10/1998 | Yu | 378/65 |
| 6,038,283 A | 3/2000 | Carol et al. | 378/65 |
| 6,038,284 A | 3/2000 | Hernandez-Guerra et al. | 378/65 |
| 6,052,430 A | 4/2000 | Siochi et al. | 378/65 |
| 6,052,435 A | 4/2000 | Hernandez-Guerra et al. | 378/150 |
| 6,134,296 A * | 10/2000 | Siochi | 378/65 |
| 6,240,161 B1 * | 5/2001 | Siochi | 378/65 |
| 6,314,159 B1 * | 11/2001 | Siochi | 378/65 |

FOREIGN PATENT DOCUMENTS

| | | | | |
|---|---|---|---|---|
| GB | 2335583 A | 9/1999 | | |
| GB | 2342552 A | 12/2000 | | |
| WO | WO 00/15299 | 3/2000 | | A61N/5/10 |

* cited by examiner

*Primary Examiner*—Robert H. Kim
*Assistant Examiner*—Allen C. Ho

(57) ABSTRACT

Systems and methods for radiation therapy planning are described. A radiation therapy includes of a series of radiation treatment fractions each including a sequence of radiation segments with a prescribed cumulative dose intensity profile to be delivered to a therapy site on a patient. In one embodiment, a pair of consecutive radiation treatment fractions is generated, wherein each fraction has a different set of radiation segments. A system, a computer program, and a computer-readable medium carrying instructions for radiation therapy planning also are described. The system, computer program, and computer-readable medium each are operable to combine common radiation segments of two radiation treatment fractions to reduce the total number of radiation segments applied to the patient.

20 Claims, 4 Drawing Sheets

RADIATION THERAPY PLANNING

CROSS-REFERENCE TO RELATED APPLICATIONS

Under 35 U.S.C. § 119, this application claims the benefit of German Application No. 10023158.6, filed May 12, 2000, and entitled "Process and Means for the Production of a Radiation Device for Carrying Out an Intensity-Modulated Radiotherapy as well as Radiation Device," which is incorporated herein by reference.

TECHNICAL FIELD

This invention relates to systems and methods for planning radiation therapy for a patient.

BACKGROUND

Radiation therapy involves delivering a high, curative dose of radiation to a tumor, while minimizing the dose delivered to surrounding healthy tissues and adjacent healthy organs. Therapeutic radiation doses typically are supplied by a charged particle accelerator that is configured to generate a high-energy electron beam. The electron beam may be applied directly to one or more therapy sites on a patient, or it may be used to generate a photon (e.g., X-ray) beam, which is applied to the patient. With a multi-leaf collimator, the shape of the radiation beam at the therapy site may be controlled by multiple leaves (or finger projections) that are positioned to block selected portions of the radiation beam. The multiple leaves may be programmed to contain the radiation beam within the boundaries of the therapy site and, thereby, prevent healthy tissues and organs located beyond the boundaries of the therapy site from being exposed to the radiation beam.

A typical radiation therapy plan calls for the delivery of series of radiation treatment fractions to the patient over the course of a several days or weeks. Each treatment fraction consists of a sequence of radiation segments with a prescribed cumulative dose intensity profile. Each segment generally has a different intensity profile and, therefore, requires a different leaf arrangement. The time required to deliver a treatment fraction primarily depends on the prescribed cumulative dose and the number of segments to be delivered to the patient. In order to reduce the discomfort patients experience during the delivery of a treatment fraction, efforts have been made to reduce the time needed to deliver treatment fractions to the patient. For example, U.S. Pat. No. 5,663,999 describes a scheme for optimizing the delivery of an intensity modulated radiation beam by selectively combining segments in a single treatment fraction to reduce the total number of segments in the treatment fraction.

SUMMARY

The invention features systems and methods of planning a radiation therapy comprising of a series of radiation treatment fractions each comprising a sequence of radiation segments with a prescribed cumulative dose intensity profile to be delivered to a therapy site on a patient.

In one aspect of the invention, a pair of consecutive radiation treatment fractions is generated, wherein each treatment fraction comprises a different set of radiation segments.

Embodiments may include one or more of the following features.

Common radiation segments of two consecutive prescribed radiation treatment fractions may be combined to reduce the total number of radiation segments applied to the patient. The resulting intensity profiles of the two consecutive radiation treatment fractions may be different.

The intensity profiles of the two consecutive radiation treatment fractions may be generated from an initial common intensity profile. The common cumulative dose intensity profile may be divided into a series of layers each corresponding to a predetermined dosage level. The layers preferably are re-assigned to a respective one of the two consecutive radiation treatment fractions. The layers may be re-assigned to the consecutive radiation treatment fractions so that the intensity profiles of the two consecutive radiation treatment fractions are approximately the same. Adjacent layers of the series of layers may be assigned to a different one of the two consecutive radiation treatment fractions. The remaining radiation treatment fractions may be grouped into fraction pairs, wherein the fractions of each pair each has a respective intensity profile generated from layers of a common intensity profile. The treatment fractions of each pair may have different intensity profiles.

The two consecutive radiation treatment fractions may be normalized. For example, the two consecutive radiation treatment fractions may be normalized by increasing the predetermined dosage level of each layer by the same amount to achieve a cumulative radiation dose for each treatment fraction that is substantially the same as the cumulative radiation dose of the common intensity profile. In one embodiment, the radiation treatment fractions may be normalized by substantially doubling the predetermined dosage level of each layer.

In one embodiment, the total number of radiation segments applied to the patient may be reduced further. In this embodiment, the intensity profile of a selected one of the two consecutive radiation treatment fractions may be divided into a plurality of radiation segments. Divided out radiation segments preferably are combined to reduce the total number of radiation segments in the selected treatment fraction.

The invention also features a system, a computer program, and a computer-readable medium carrying instructions for planning the application of a series of radiation treatment fractions, each fraction comprising a sequence of radiation segments with a prescribed cumulative dose intensity profile to be delivered to a therapy site on a patient. The system, computer program, and computer-readable medium each are operable to combine common radiation segments of two radiation treatment fractions to reduce the total number of radiation segments applied to the patient.

Among the advantages of the invention are the following.

The invention combines common radiation segments across the series of the radiation treatment fractions in the overall treatment plan to reduce the total number of segments in each treatment fraction. In accordance with this inventive scheme, the treatment time may be reduced without substantially changing the overall, curative biological effect of the treatment plan.

Other features and advantages of the invention will become apparent from the following description, including the drawings and the claims.

DETAILED DESCRIPTION

Figure 1:
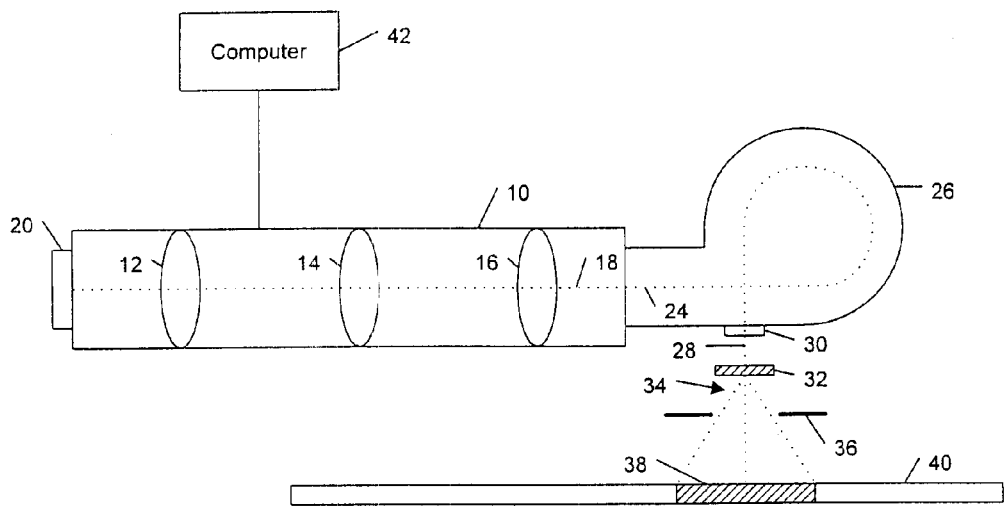
FIG. 1 is a block diagram of a radiation treatment device delivering a therapeutic radiation beam to a therapy site on a patient.
Figure 2:
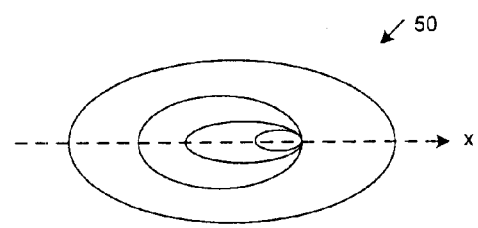
FIG. 2 is a diagrammatic topological view of a treatment fraction intensity profile.
Figures 3A, 3B, 3C, 3D:
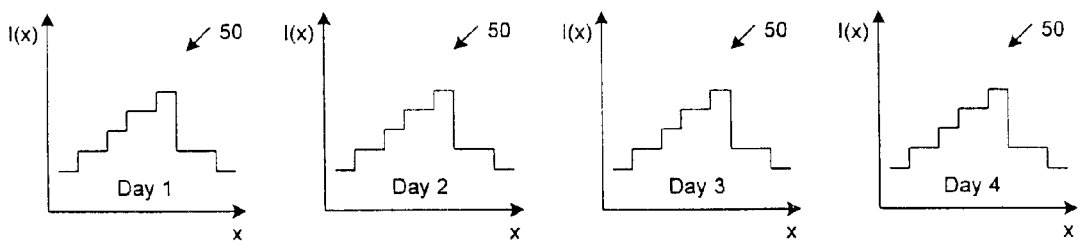
FIGS. 3A–3D are diagrammatic one-dimensional intensity profile plots in a conventional treatment plan consisting of the delivery of the treatment fraction of FIG. 2 to a therapy site on a patient on each of four consecutive days.

Referring to FIG. 1, a conventional charged particle accelerator 10 for use in a medical radiotherapy device includes a series of accelerating cavities 12, 14, 16 that are aligned along a beam axis 18. A particle source 20 (e.g., an electron gun) directs charged particles into accelerating cavity 12. As the charged particles travel through the succession of accelerating cavities 12–16, the particles are focused and accelerated by an electromagnetic field that is applied by an external source. The resulting accelerated particle beam 24 may be directed to a magnetic energy filter 26 that bends beam 24 by approximately 270°. A filtered output beam 28 is directed through a window 30 to a target 32 that generates a photon beam 34. The intensity of radiation beam 34 typically is constant. One or more adjustable leaves 36 may be positioned to block selected portions of radiation beam 34 to conform the boundary of radiation beam 34 to the boundaries of a therapy site 38 on a patient 40. A computer 42 typically is programmed to control the operation of leaves 36 to generate a prescribed intensity profile over the course of a treatment.

A conventional treatment plan for curing, for example, a tumor on a patient, typically involves delivering several treatment fractions to the therapy site over the course of several days. The goal of the treatment plan is to deliver a high curative dose to the tumor, while minimizing the dose received by normal tissues. The cumulative dose that may be delivered to a patient at any given time typically is limited by the radiation dose tolerance of critical healthy structures near the therapy site. The process of delivering an optimal treatment that conforms to the shape of the tumor typically involves modulating the intensity of the radiation beam across the beam dimension (i.e., perpendicular to the beam axis). Modulation of the beam intensity is achieved by dividing the beam into a sequence of radiation segments each having a uniform intensity profile and a different beam shape, each shape being defined by the programmed position of leaves 36. As shown in FIGS. 3A–3D, conventionally, after an oncologist has determined the optimal intensity profile and the optimal curative dose for treating the tumor, the same radiation intensity profile 50 is delivered to the patient at the dose tolerance limit once per day until the cumulative dose delivered to the tumor reaches the prescribed, optimal curative dose.

As mentioned above, it is highly desirable to reduce the time required to administer each treatment fraction. In one embodiment of the invention, this result is achieved by combining (or grouping) common radiation segments across the series of the radiation treatment fractions in the overall treatment plan to reduce the total number of segments in each treatment fraction. As described in detail below, in accordance with this embodiment, the treatment time may be reduced without substantially changing the overall, curative biological effect of the treatment plan.

Figure 4:
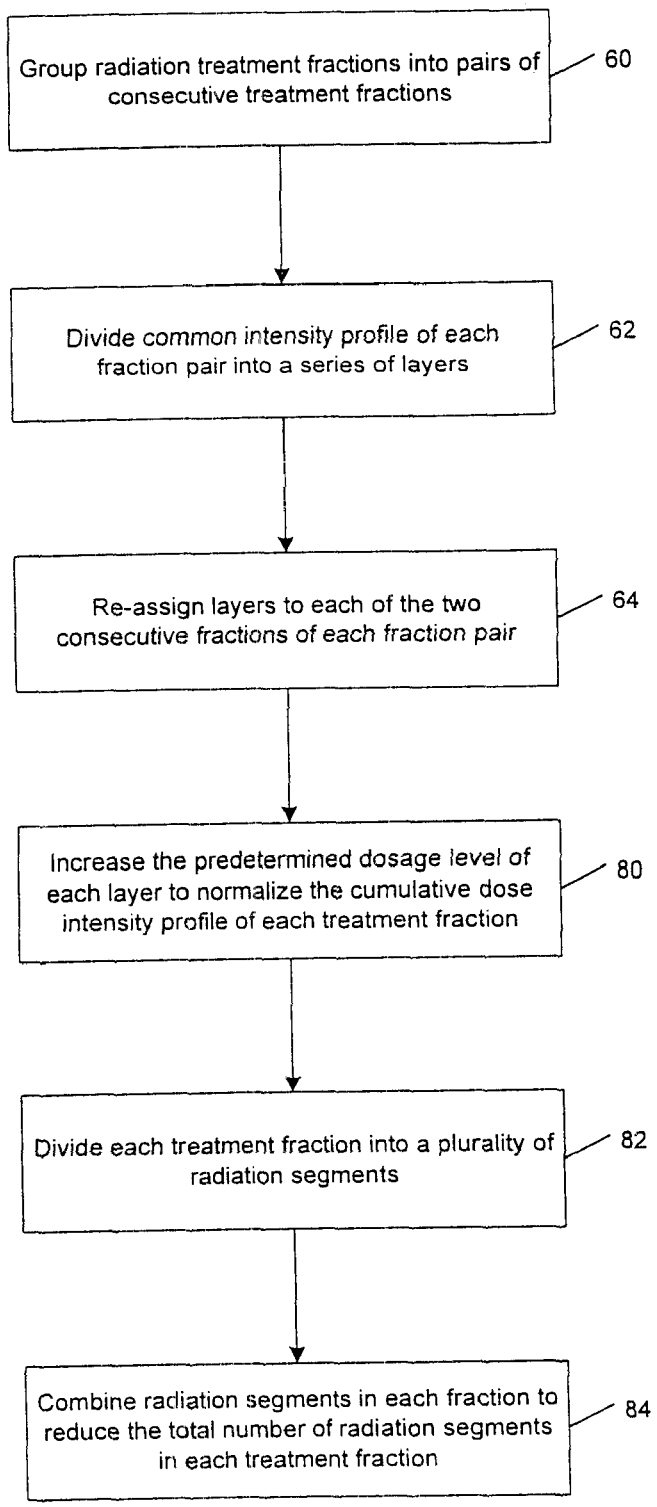
FIG. 4 is a flow diagram of a method of planning a course of radiation therapy.
Figure 5:
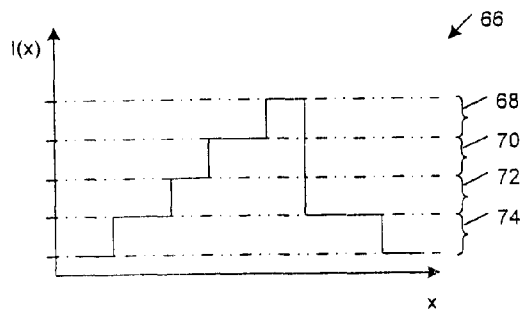
FIG. 5 is a diagrammatic one-dimensional plot of an intensity profile of a treatment fraction divided into a series of four layers.
Figure 6A:
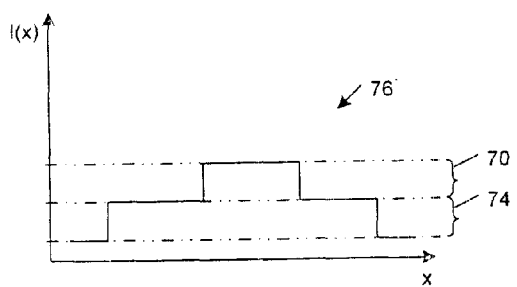
FIGS. 6A and 6B are diagrammatic one-dimensional plots of partial intensity profiles generated from the intensity profile of FIG. 5.
Figure 6B:
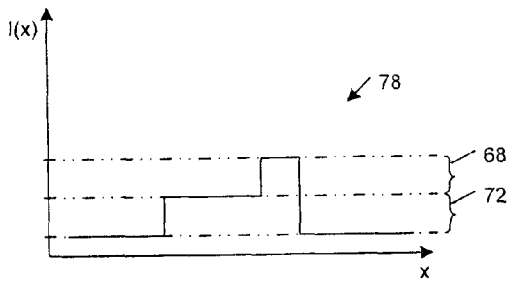

Referring to FIG. 4, in one embodiment, the total number of radiation segments delivered to a patient over the course of a treatment plan may be reduced as follows. Radiation treatment fractions are grouped into pairs of consecutive treatment fractions (step 60). In this embodiment, the fractions of each fraction pair are assumed to have the same initial common intensity profile; although, in other embodiments, each treatment fraction may have a different initial intensity profile. The common intensity profile of each fraction pair is divided into a series of layers (step 62). Each layer, for example, may correspond to 1 MU (Monitor Unit) of intensity. Thus, if a common intensity profile has a maximum intensity of N MU, it may be divided into N layers. Layers are re-assigned to each of the two consecutive treatment fractions of each fraction pair (step 64). Layers may be re-assigned to the two consecutive treatment fractions of each fraction pair in a variety of ways. For example, as shown in FIGS. 5, 6A and 6B, a common intensity profile 66 may be divided into four layers 68, 70, 72, 74. In one embodiment, adjacent layers of common intensity profile 66 may be re-assigned to a different one of consecutive treatment fractions 76, 78. Thus, treatment fraction 76 may consist of non-adjacent layers 70, 74, and treatment fraction 78 may consist of non-adjacent layers 68, 72. Typically, this method of assigning layers results in treatment fractions 76, 78 that are substantially similar to each other and substantially similar to the original, common intensity profile 66.

Figure 7A:
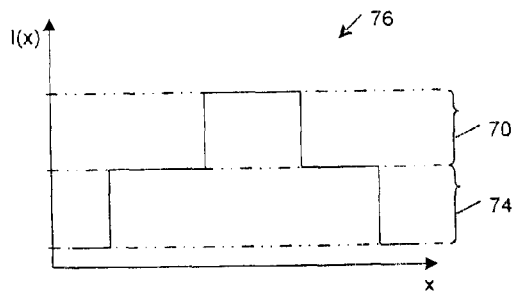
FIGS. 7A and 7B are diagrammatic one-dimensional plots of the partial intensity profiles of FIGS. 6A and 6B, respectively, normalized to the cumulative dose of the treatment fraction of FIG. 5.
Figure 7B:
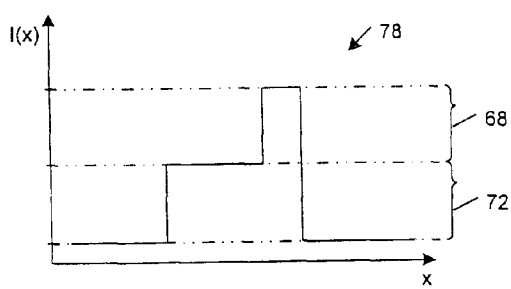
Figure 8:
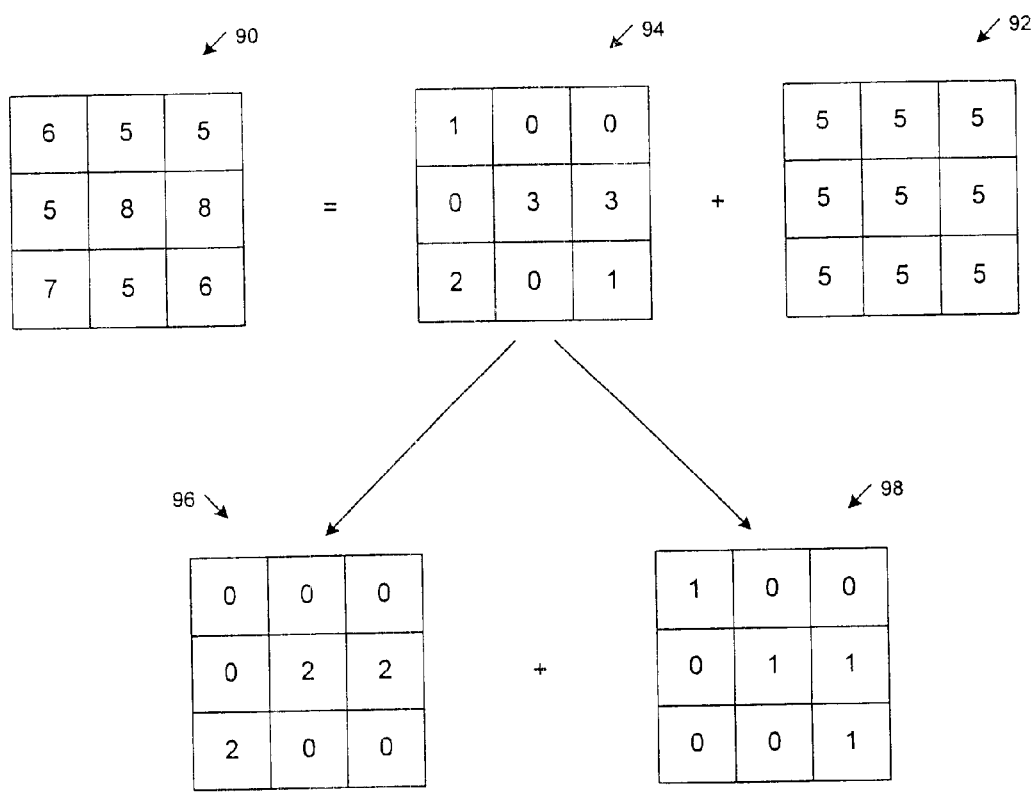
FIG. 8 is a diagrammatic view of matrices illustrating a method of reducing the total number of radiation segments in a treatment fraction.

Next, as shown in FIGS. 7A and 7B, the predetermined dosage level (e.g., 1 MU) of each layer 68–74 is increased uniformly to normalize the cumulative dose intensity profile of each treatment fraction 76, 78 (step 80). Typically, the cumulative dose of each treatment fraction 76, 78 is normalized to the cumulative dose (e.g., the dose tolerance limit) of the common intensity profile 66. The resulting normalized treatment fractions 76, 78 have a reduced number of segments relative to the number of segments in the initial treatment fractions 66 without substantially changing the curative, biological effect of the overall treatment plan. For example, assuming each layer 68–74 of the common treatment fraction 66 corresponds to a respective segment, each of the original, unmodified treatment fractions would have four segments, whereas each of the modified treatment fractions 76, 78 has only two segments. Thus, in this example, the total number of segments delivered to the patient for each treatment fraction would be reduced by 50%. In effect, the inventive method described herein combines common segments of consecutive treatment fractions in each fraction pair to reduce the total number of segments in each treatment fraction. Because a significant portion of the treatment time is devoted to adjusting the collimator leaves to conform to the required shapes of the segments, this segment reduction method reduces the total treatment time by a significant amount.

The resulting treatment fractions 76, 78 may be applied to the patient directly, or the number of segments in each treatment fraction may be reduced further. In one embodiment, the number of segments in each treatment fraction is further reduced by dividing each treatment fraction into a plurality of radiation segments (step 82), and combining two or more of the common segments within each treatment fraction (step 84).

As explained in U.S. Pat. No. 5,663,999, which is incorporated herein by reference, in accordance with one intra-fraction segment reduction method, a treatment fraction intensity profile may be represented as a matrix 90 of intensity values arranged in accordance with the spatial locations of the treatment fraction intensity profile. In the first step of the intra-fraction segment reduction method, matrix 90 is divided into a uniform matrix 92 containing the highest uniform intensity values that may be extracted from matrix 90, and a variation matrix 94 representing the difference between matrix 90 and uniform matrix 92. Uniform matrix 92 corresponds to a single segment because a single leaf arrangement is required to generate the intensity profile represented by matrix 92. Variation matrix 94, on the other hand, corresponds to three segments because three different leaf arrangements are required to generate the intensity profile represented by matrix 94. In a second step of the intra-treatment segment reduction method, the number of segments of variation matrix 94 is reduced by generating the minimum number of uniform matrices 96, 98 with a sum that equals variation matrix 94. The intensity profile of each of the uniform matrices 96, 98 may be generated by a single leaf arrangement and, consequently, each uniform matrix 96, 98 corresponds to a single segment. Thus, the fraction profile of matrix 90 may be generated by only three segments (corresponding to matrices 92, 96, and 98), as opposed to the four or more segments that otherwise would have been required if common segments within matrix 90 were not combined.

Other computational techniques also may be used to further reduce the total number of segments in each treatment fraction.

The systems and methods described herein are not limited to any particular hardware or software configuration, but rather they may be implemented in any computing or processing environment. The multi-leaf controller program operating within computer 42 preferably is implemented in a high level procedural or object oriented programming language; however, the program may be implemented in assembly or machine language, if desired. In any case, the programming language may be a compiled or interpreted language. In addition, the multi-leaf controller program may be configured to reduce the number of segments in a prescribed treatment plan based upon an initial series of oncologist-prescribed treatment fractions. Alternatively, the program may be integrated with the initial treatment fraction generation system so that the final reduced-segment treatment fractions may be generated on the fly, without requiring an initial series of prescribed treatment fractions.

Other embodiments are within the scope of the claims.

What is claimed is:

1. A method of planning a radiation therapy comprising of a series of radiation treatment fractions each comprising a sequence of radiation segments with a prescribed cumulative dose intensity profile to be delivered to a therapy site on a patient, the method comprising generating a pair of consecutive radiation treatment fractions each comprising a different set of radiation segments.

2. The method of claim 1, further comprising combining common radiation segments of two prescribed radiation treatment fractions to reduce the total number of radiation segments applied to the patient.

3. The method of claim 2, wherein common radiation segments of two consecutive prescribed radiation treatment fractions are combined to reduce the total number of radiation segments applied to the patient.

4. The method of claim 3, wherein the resulting intensity profiles of the two consecutive radiation treatment fractions are different.

5. The method of claim 4, further comprising generating the intensity profiles of the two consecutive radiation treatment fractions from an initial common intensity profile.

6. The method of claim 5, further comprising dividing the common cumulative dose intensity profile into a series of layers each corresponding to a predetermined dosage level.

7. The method of claim 6, further comprising assigning the layers to a respective one of the two consecutive radiation treatment fractions.

8. The method of claim 7, further comprising normalizing the two consecutive radiation treatment fractions.

9. The method of claim 8, wherein the two consecutive radiation treatment fractions are normalized by increasing the predetermined dosage level of each layer by the same amount to achieve a cumulative radiation dose for each treatment fraction that is substantially the same as the cumulative radiation dose of the common intensity profile.

10. The method of claim 9, wherein the two consecutive radiation treatment fractions are normalized by substantially doubling the predetermined dosage level of each layer.

11. The method of claim 8, further comprising dividing the intensity profile of a selected one of the two consecutive treatment fractions into a plurality of radiation segments.

12. The method of claim 11, further comprising combining divided out radiation segments to reduce the total number of radiation segments in the selected treatment fraction.

13. The method of claim 8, wherein the layers are assigned to the consecutive radiation treatment fractions so that the intensity profiles of the two consecutive treatment fractions are approximately the same.

14. The method of claim 13, wherein adjacent layers of the series of layers are assigned to a different one of the two consecutive treatment fractions.

15. The method of claim 13, wherein the remaining treatment fractions are grouped into fraction pairs, wherein the fractions of each fraction pair each has a respective intensity profile generated from layers of a common intensity profile.

16. The method of claim 15, wherein the fractions of each fraction pair have different intensity profiles.

17. A system for planning the application of a series of radiation treatment fractions each comprising a sequence of radiation segments with a prescribed cumulative dose intensity profile to be delivered to a therapy site on a patient, the system comprising a computer operable to combine common radiation segments of two radiation treatment fractions to reduce the total number of radiation segments applied to the patient.

18. A computer-readable medium carrying instructions for planning the application of a series of radiation treatment fractions each comprising a sequence of radiation segments with a prescribed cumulative dose intensity profile to be delivered to a therapy site on a patient, the instructions comprising the step of combining common radiation segments of two radiation treatment fractions to reduce the total number of radiation segments applied to the patient.

19. A computer program for planning the application of a series of radiation treatment fractions each comprising a sequence of radiation segments with a prescribed cumulative dose intensity profile to be delivered to a therapy site on a patient, the computer program residing on a computer-readable medium and comprising computer-readable instructions for causing a computer to combine common radiation segments of two radiation treatment fractions to reduce the total number of radiation segments applied to the patient.

20. A system for delivering a series of radiation treatment fractions each comprising a sequence of radiation segments with a prescribed cumulative dose intensity profile to be delivered to a therapy site on a patient, the system comprising:

a radiotherapy device configured to generate a sequence of radiation segments; and a computer programmed to combine common radiation segments of two radiation treatment fractions to reduce the total number of radiation segments applied to the patient, the computer being further programmed to control the delivery of radiation segments to the patient.

* * * * *